(12) United States Patent
Seneci et al.

(10) Patent No.: US 7,838,030 B2
(45) Date of Patent: Nov. 23, 2010

(54) COMPOSITIONS FOR ORAL USE BASED ON S-ADENOSYLMETHIONINE AND A PROCESS FOR THEIR PREPARATION

(75) Inventors: Alessandro Seneci, Segrate (IT); Daniele Giovannone, Frosinone (IT); Cesare Zio, Milan (IT)

(73) Assignee: Graal SR:L (IT)

( * ) Notice: Subject to any disclaimer, the term of this patent is extended or adjusted under 35 U.S.C. 154(b) by 0 days.

(21) Appl. No.: 11/276,900

(22) Filed: Mar. 17, 2006

(65) Prior Publication Data
US 2007/0160660 A1 Jul. 12, 2007

(30) Foreign Application Priority Data
Jan. 10, 2006 (IT) .......................... MI2006A0026

(51) Int. Cl.
*A61K 9/20* (2006.01)
(52) U.S. Cl. .................................................... 424/464
(58) Field of Classification Search ........................ None
See application file for complete search history.

(56) References Cited

U.S. PATENT DOCUMENTS

| | | | | |
|---|---|---|---|---|
| 2,824,869 | A | | 2/1958 | Buckwalter et al. |
| 3,019,167 | A | * | 1/1962 | Innerfield ................. 424/94.64 |
| 4,028,183 | A | * | 6/1977 | Fiecchi .......................... 435/88 |
| 4,284,630 | A | * | 8/1981 | Yu et al. ...................... 514/179 |
| 6,417,196 | B1 | * | 7/2002 | Daniel et al. ................. 514/310 |
| 2001/0033872 | A1 | * | 10/2001 | Corson et al. ................ 424/730 |
| 2001/0043945 | A1 | * | 11/2001 | Addicks et al. ............. 424/461 |
| 2003/0078231 | A1 | | 4/2003 | Wilburn |
| 2003/0144244 | A1 | | 7/2003 | Herbert |
| 2004/0043013 | A1 | * | 3/2004 | McCleary .................. 424/94.1 |
| 2004/0234587 | A1 | | 11/2004 | Sampalis |

FOREIGN PATENT DOCUMENTS

| | | |
|---|---|---|
| WO | WO 01/55083 | 8/2001 |
| WO | WO 03/043608 | 5/2003 |
| WO | WO 2007/004244 | 1/2007 |

OTHER PUBLICATIONS

"S-adenosylmethionine". The Merck Index, Fourteenth Edition. Online. Accessed on Feb. 27, 2007. <http://themerckindex.cambridgesoft.com>.*
"Handbook of Pharmaceutical Excipients", 1986, American Pharmaceutical Association and the Pharmaceutical Society of Great Britain, pp. 251-252.*
"Shellac". Handbook of Pharmaceutical Excipients, 1986 Ed., American Pharmaceutical Association and the Pharmaceutical Society of Great Britain, pp. 251-252.*
"Magnesium oxide". Handbook of Pharmaceutical Excipients, 5th Ed. Apr. 26, 2005. American Pharmaceutical Association and Pharmaceutical Press, pp. 426-427.*
L. W. Parks and F. Schlenk, The Stability and Hydrolysis of S-Adenosylmethionine; Isolation of S-RiboSylmethionine, J. Biol. Chem., 230:295-305 (1958).
Morana A et al, "Stabilization of S-adenosyl-L-methionine promoted by trehalose," Biochimica et Biophysica ACTA, vol. 1573, No. 2, Nov. 14, 2002, pp. 105-108, XP002354153 ISSN: 0006-3002, Amsterdam, NL.
International Search Report for PCT/EP2006/068533, EPO, Jul. 19, 2007.
Written Opinion of the International Search Authority for PCT/EP2006/068533, EPO, Oct. 7, 2008.
International Preliminary Report on Patentability for PCT/EP2006/068533, International Bureau of WIPO, Jul. 15, 2008, Geneva, Switzerland.

* cited by examiner

*Primary Examiner*—Robert A Wax
*Assistant Examiner*—Bethany Barham
(74) *Attorney, Agent, or Firm*—Stephen Nipper; Elizabeth Herbst Schierman

(57) ABSTRACT

The present invention relates to solid dietary and/or nutraceutic pharmaceutical compositions for oral use based on SAMe, or salts thereof, in combination with inositol and/or derivatives thereof and to a process for their preparation.

The present invention relates to a method of stabilising a solid composition for oral use based on SAMe or salts thereof, making use of inositol and/or derivatives thereof with the addition of magnesium oxide.

28 Claims, No Drawings

COMPOSITIONS FOR ORAL USE BASED ON S-ADENOSYLMETHIONINE AND A PROCESS FOR THEIR PREPARATION

CROSS-REFERENCE TO RELATED APPLICATIONS

This application is a non-provisional application which claims the priority date from the Italian patent application entitled Compositions For Oral Use Based on S-adenosylmethionine and a Process For Their Preparation filed by Seneci, et al. on Jan. 10, 2006 with application number MI 2006 A 000026, the disclosure of which is incorporated herein by reference.

FIELD OF THE INVENTION

The present invention relates to solid dietary and/or nutraceutic pharmaceutical compositions for oral use based on SAMe, or salts thereof, in combination with inositol and/or derivatives thereof and to a process for their preparation.

The present invention relates to a method of stabilising a solid composition for oral use based on SAMe or salts thereof, making use of inositol and/or derivatives thereof with the addition of magnesium oxide.

The present invention also relates to the use of SAMe, or salts thereof, in combination with inositol and/or derivatives thereof with the possible further addition of St. John's Wort and/or lemon balm for the treatment of depressive states and/or panic syndromes.

SUMMARY OF THE INVENTION

S-adenosylmethionine (SAMe) is a physiological methyl donor which is present in every living organism and is used in enzymatic transmethylation reactions.

Accordingly, this substance plays a role of considerable biological importance and is used clinically mainly as an antidepressant.

However, it is known that S-adenosylmethionine is difficult to use as a pharmaceutical and/or dietary substance due to the fact that it is extremely unstable at temperatures above 0° C. or in the presence of moisture.

Accordingly, formulations based on S-adenosylmethionine, if not formulated using particular procedures and specific measures, reflect the aforementioned instability of the active component which has obvious adverse effects on the preservation and storage of the product, even over limited periods of time.

US patent specifications U.S. Pat. No. 3,954,726 and U.S. Pat. No. 4,057,672 describe salts of S-adenosylmethionine which are relatively stable up to 25° C. and 45° C., respectively. US patent specification U.S. Pat. No. 4,465,672 furthermore describes stable salts of S-adenosylmethionine with 5 moles of a sulphonic acid having a pK below 2.5.

In said latter US patent specification, the process for the preparation of the product comprises preparing a concentrated aqueous solution of an untreated SAMe salt, purifying said solution and eluting it with a dilute aqueous solution of the preselected sulphonic acid, titrating the resulting eluate, concentrating it and lyophilising or spray-drying it. Owing to the high instability of SAMe and its derivatives, the use of an aqueous medium reveals the limits of such a process, which, even if is possible to limit the residual moisture, is still inadequate due to the characteristics of the active component.

Up to now, there are no known methods for stabilising and preserving S-adenosylmethionine salts in solid oral formulations, in particular in tablets. The only known concept is that the moisture and impurities must be strictly controlled, and the tablets must be protected by film coating.

Accordingly, there is now felt to be a need for indicating a simple and economical process, which allows the preparation of a product which is based on SAMe and exhibits reduced hygroscopicity and thus increased stability.

Surprisingly, it has been found that the addition of inositol and/or derivatives thereof gives improved stability and reduced hygroscopicity of the SAMe, favouring moreover a synergic calming and antidepressant action.

Accordingly, the present invention relates to solid dietary and/or nutraceutic oral pharmaceutical compositions comprising SAMe, or salts thereof, in combination with inositol and/or derivatives thereof and pharmaceutically acceptable excipients.

According to the present invention, "SAMe" is understood to mean either the racemic mixture or the individual diastereomers (RS)-(+)-S-adenosyl-L-methionine [(RS)-(+)-SAMe)] and (SS)-(+)-S-adenosyl-L-methionine [(SS)-(+)-SAMe)], including mixtures different from the racemic one.

In particular, the compositions according to the present invention contain SAMe, or salts thereof, in an amount of between 10 and 90% by weight, preferably between 10 and 50% by weight, relative to the weight of the composition, in combination with inositol and/or derivatives thereof in an amount of between 50 and 90% by weight, preferably between 30 and 85% by weight, relative to the weight of the composition.

Preferably, said SAMe and/or salts thereof is S-adenosylmethionine para-toluenesulphonate.

Preferably, said inositol and/or derivatives thereof is inositol on its own, inositol 6-phosphate or a mixture thereof.

In addition, according to a preferred aspect, at least one of the pharmaceutically acceptable excipients of the present invention is magnesium oxide.

Optionally, the compositions according to the present invention can contain at least one other active component, preferably selected from a St John's Wort dry extract or essential oil and/or a lemon balm dry extract or essential oil and/or other extracts or essential oils having a tranquilising pharmacological action.

The compositions according to the present invention can be in the form of tablets, capsules, granules and/or powders. Preferably, the compositions according to the present invention are in the form of tablets, more preferably simple, coated, film-coated, layered and/or gastroresistant tablets.

In the present invention, a simple tablet is understood to mean a tablet obtained by direct compression or by compression following granulation without coating; a coated tablet is understood to mean a tablet coated with non-gastroresistant substances; a film-coated tablet is understood to mean a coated tablet covered subsequently with aqueous varnishes, in which the varnishes can have a gastroresistant action. A layered tablet is understood to mean a tablet with two or three layers, obtained in a suitable tablet compressing machine.

Therefore, the compositions according to the present invention can be film-coated with aqueous varnishes, preferably selected from gum lac (Shellac™) and/or salts thereof, methacrylic acid, cellulose acetophthalates, titanium dioxide, talcum, triethyl citrate, PVP K30, riboflavin 6-phosphate, hydroxypropylcellulose, hydroxypropylmethyl-cellulose and/or mixtures thereof.

A gastroresistant tablet according to the present invention is understood to mean a tablet capable of passing the gastric barrier unaltered.

Said film-coating by means of varnishes, when effected with Shellac™ salts, cellulose acetophthalates and/or other coatings insoluble in acidic media, can make the compositions according to the invention resistant when passing through the gastric barrier. The varnish according to the present invention can be present in an amount which varies from 2.0 to 8.0% by weight, relative to the composition.

During said film-coating with aqueous varnishes, a lemon balm oil or St. John's Wort oil can be added in an amount of between 0.01 and 0.2% by weight, calculated relative to the total weight of the tablet.

The compositions according to the present invention are about eight times less hygroscopic compared with the previously known compositions based on SAMe, as reported in Table 1 below.

TABLE 1

| Known tablets based on SAMe SAMe tablet 200 mg KF % T = 0 | Known tablets based on SAMe SAMe tablet 200 mg KF % T = 24 h* | SAMe/Inositol tablets (Example 1) KF % T = 0 | SAMe/Inositol tablets (Example 1) KF % T = 24 h* |
|---|---|---|---|
| Batch 01 1.55 | 3.42 | 0.80 | 0.93 |
| Batch 02 1.44 | 3.24 | 0.74 | 0.89 |
| Batch 03 1.47 | 3.14 | 0.72 | 0.89 |
| Batch 04 1.56 | 3.42 | 0.73 | 0.94 |
| Batch 05 1.61 | 3.09 | 0.81 | 1.04 |

*at 40° C. and 75% of r.h. KF (moisture determination by the Karl Fischer method)
*T = time The compositions according to the present invention are preferably intended for the treatment of depressive states and panic-related syndromes.

Another object of the present invention is a process for the preparation tablets for oral use comprising SAMe, or salts thereof, in combination with inositol and/or derivatives thereof, which comprises the steps of:
 a) mixing SAMe, or salts thereof, with pharmaceutically acceptable excipients;
 b) pre-compression, followed by granulation, of the mixture obtained in step a);
 c) coating the granules obtained in step b) with hydrogenated fatty acids;
 d) mixing, pre-compression and granulation of inositol and/or derivatives thereof with pharmaceutically acceptable excipients;
 e) coating the granules obtained in step d) with hydrogenated fatty acids;
 f) mixing the granules obtained in steps c) and e) with pharmaceutically acceptable excipients;
 g) compression of the mixture obtained in step f), with the optional addition of sweeteners and/or aromatic substances;
 h) optionally coating the tablets obtained in step g) with hydrogenated fatty acids;
 i) optionally film-coating in the aqueous phase the tablets obtained in step h).

The process according to the present invention is carried out in an environment in which the relative humidity is below 25% and the temperature is maintained between 20 and 30° C., preferably at about 25° C.

The granulation according to the present invention is preferably carried out in a vibrating granulator equipped with a perforated stainless steel plate with holes 1 to 2 mm in diameter.

SAMe, or salts thereof, is used in an amount varying between 10 and 90% by weight, relative to the weight of the composition, preferably between 10 and 50% by weight.

In particular, the pharmaceutically acceptable excipients used in the process according to the invention are preferably selected from magnesium oxide, anhydrous microcrystalline cellulose, hydrogenated fatty acids, magnesium stearate, glyceryl behenate, hydrogenated palm oil and hydrogenated castor oil.

More particularly, in step a), the active component is preferably mixed with about 1.0 to about 10.0% by weight of magnesium oxide and/or about 1.0 to about 20.0% by weight of microcrystalline cellulose and/or about 1.0 to about 30.0% by weight of hydrogenated fatty acids and/or about 0.5 to about 5% by weight of magnesium stearate, calculated relative to the active component.

In step c), the coating by means of hydrogenated fatty acids, preferably, melted hydrogenated vegetable fatty acids, can take place by conventional processes known in this sector, such as, for example by a process comprising the steps of:
 (1) coating with melted hydrogenated fat, if desired with the addition of surfactants which are miscible in the oily liquid. The addition of the melt takes place continuously by means of a peristaltic pump, preferably by means of an airless atomiser at a flow rate of between 50 and 2000 g/min, preferably between 200 and 1000 g/min. The temperature of the mass to be coated is between 20° and 60° C., preferably between 35° and 55° C.;
 (2) if desired, subsequently coating the granules with pH-dependent pulverulent substances using in each case the previously selected mixer. Such substances are added in an amount of between 2% and 10% by weight, preferably between 3% and 5%;
 (3) separating off, for example on a vibrating sieve, any agglomerates which may have formed during the coating.

In step d), inositol and/or derivatives thereof are preferably mixed with glyceryl behenate and/or hydrogenated palm oil and/or hydrogenated castor oil and/or stearic acid contained in an amount of between about 2 and about 30% by weight, calculated relative to inositol and/or salts thereof and/or derivatives thereof.

Optionally, in said step d) of the process according to the invention, at least one further active component, preferably selected from St. John's Wort dry extract and lemon balm dry extract and/or mixtures thereof, can be added to the mixture.

In step e), the coating with hydrogenated fatty acids, preferably melted hydrogenated vegetable fatty acids, can be carried out by conventional processes, known in the sector, such as, for example, the process which comprises the same steps listed above in step c).

According to the present invention, the coating described in step h) can be carried out with hydrogenated fatty acids, preferably melted hydrogenated vegetable fatty acids, in an amount of between about 0.5 and about 2.5% by weight, relative to the weight of the composition.

Said step h) of the process according to the present invention allows about a two-fold reduction of the hygroscopicity of the tablets obtained in g), resulting in significant advantages in the optional subsequent step of film-coating in the aqueous phase.

The film-coating in the aqueous phase (step i) can be carried out with a substance or varnish preferably selected from gum lac and/or salts thereof (Shellac™), methacrylic acid, cellulose acetophthalates, titanium dioxide, talcum, triethyl citrate, PVP K30, riboflavin 6-phosphate, hydroxypropylcellulose, hydroxypropylmethylcellulose and/or mixtures thereof.

In particular, said film-coating can be carried out with substances preferably selected from gum lac (Shellac™) and/or salts thereof.

It is possible to add, to the varnish, lemon balm oil and/or St. John's Wort oil in an amount which varies between 0.01 and 0.2% by weight, relative to the total weight of the composition.

Another object of the present invention is the use of SAMe, or salts thereof, in combination with inositol and/or derivatives thereof for the preparation of dietary and/or nutraceutic pharmaceutical compositions for the treatment of depressive states and/or panic-related syndromes.

Yet another object of the present invention is a method of stabilising solid compositions for oral use based on SAMe or salts thereof, which comprises using inositol and/or derivatives thereof in the previously mentioned percentages.

EXAMPLE 1

Tablets Containing 100 mg of SAMe Ion/Tablet

Composition Based on SAMe Sulphate p-toluenesulphonate/Inositol

| | | |
|---|---|---|
| A. SAMe sulphate p-toluenesulphonate | 215.00 mg | |
| B. Inositol | 1000.00 mg | |
| C. Magnesium oxide | 50.00 mg | |
| D. Glyceryl behenate (Compritol-e-ato ®) | 100.00 mg | |
| E. Anhydrous microcrystalline cellulose | 70.00 mg | |
| F. Magnesium stearate | 10.00 mg | |
| Total weight of the core | 1445.00 mg | |
| G. Hydrogenated vegetable fatty acids | 8.00 mg | |
| H. Water-soluble Shellac ® | 30.00 mg | |
| I. PVP K 30 | 6.0 mg | |
| L. Titanium dioxide | 5.00 mg | |
| M. Talcum | 10.00 mg | |
| N. Triethyl citrate | 5.00 mg | |
| O. Riboflavin 6-phosphate | 0.050 mg | |
| Total weight of the tablet | 1509.05 mg | |

1.1. Mixing. The working environment is conditioned to a temperature of 25° C. and to a relative humidity value of about 25% of r.h. This is followed by transferring A, C, E and 50% of F in the amounts listed above to the mixer and stirring the resulting mixture for about 30 minutes. Upon completion of this operation, the resulting mixture is transferred to dry containers with constant control of humidity and temperature.

1.2. Pre-compression. The mixture is then pre-compressed in a Ronchi AM rotary tabletting machine equipped with 18 round 25.0 mm punches. The hardness of the tablets produced must be regulated in such as to produce subsequently a granular product with good rheological properties.

1.3 Granulation. The tablets produced during the first processing stage are granulated on 500-1200 µm meshes in each case in an environment with controlled humidity.

1.4 Coating. The granules obtained in step 1.3 are covered with a coating of melted hydrogenated vegetable fatty acids to give the granular product A.

1.5 Coating of inositol. Inositol is granulated by pre-compression with 50% of the magnesium stearate remaining from step 1.1 and then coated with melted hydrogenated vegetable fatty acids to give the granules B.

1.6 Mixing. The granular products A and B are transferred to the mixer in the amounts listed above with the addition of microcrystalline cellulose and half of the magnesium stearate (F), and the resulting mixture is stirred for about 30 minutes. Upon completion of said operation, the resulting mixture is transferred to dry containers.

1.7 Compression. The final compression of the granular products is performed by means of a Ronchi AM rotary tabletting machine equipped in each case with 18 oblong 21.0×9.8 mm punches, while regulating the weight to 1445 mg/tablet and the compression force to at least 20 kp. The tablets produced have a hardness of between 16 and 22 kp.

Friability: ≦1.0%; Disaggregation time: ≦15 minutes (measured by the methodology described in U.S.P. XXIV ed.).

Moisture by K.F.≦2.0%

Variation of the average weight: 1372.7-1517.2 mg

Standard processing yield (ratio of the weight of the cores produced in stage 1.7 to the overall weight of the initially weighed starting materials): 97%.

The stability tests on the uncoated tablets were only carried out at 40° C. and 75% of r.h. over a period of six months and for a single batch since they were not finished products. The samples were kept in alu/alu blister packs.

TABLE 2

Batch 055 - cores containing 100 mg of SAMe ion/tablet (qualitative/quantitative composition as in Example 1)

| Batch (T/t)[1] | Moisture in % (K. Fischer) | AD[2] (%) | MTAD[3] (%) | SAMe[4] |
|---|---|---|---|---|
| 055 (20/0) | 1.11 | 0.23 | 0.65 | 107.01 |
| 055A (40/1) | 1.02 | 0.65 | 1.34 | 105.58 |
| 055B (40/3) | 1.03 | 0.95 | 1.67 | 105.02 |
| 055C (40/6) | 1.05 | 1.45 | 2.32 | 104.23 |

[1]Temperature (° C.)/time (months);
[2]adenosine;
[3]methylthioadenosine;
[4]SAMe sulphate p-toluenesulphonate (mg/tablet).

The data in Table 2 show that the tablets have optimum stability.

1.8: Coating of the tablets. The tablets resulting from the preceding processing stages are coated in a drum mixer with a mixture of hydrogenated fatty acids (8.0 mg/tablet).

The hydrogenated fatty acid obtained in the melting step at 70° C. is poured into a 2-litre glass vessel, and the temperature of the mixture is brought to about 75° C., resulting in a homogeneous melt.

After the drum mixer has been preheated to about 65° C., about 250 kg of tablets are introduced and allowed to heat up to 60° C. This is followed by protection of the cores performed by pouring the previously prepared melt onto the moving tablets. The cores thus treated are left again at 60° C. for about 3 minutes, until the drum of the drum mixer is completely free of the wax layer.

1.9: Film-coating of the tablets. Shellac™ and PVP are dissolved in a container of suitable size at 50° C. to give a 20% (w/v) strength solution, and the triethyl citrate is slowly added with constant stirring.

In a different steel container, again equipped with a stirrer, the talcum, titanium dioxide and riboflavin 6-phosphate are dispersed in 4.0 l of deionised water. The resulting suspension is poured into the Shellac™ solution, the container is rinsed with about 1.0 l of deionised water, and the resulting mixture is diluted subsequently with another 4.0 l of deionised water.

During the first coating stage, the temperature of the cores is maintained at 54° C. for about 40 minutes, and subsequently and at regular intervals, is lowered until the value of 50° C. is reached in the final stage.

Once the coating of the protected cores is completed, they are allowed to dry for another 10 minutes while maintaining them at 50° C. Finally, the temperature is allowed to drop to 45-46° C., at which point the emptying of the drum mixer can be started, taking care that the tablets are kept in suitable covers impermeable to moisture. On the tablets thus obtained, no increase in the percentage moisture content was observed. Moreover, all checks stipulated in the quality specifications were carried out on the tablets.

EXAMPLE 2

Tablets Containing 100 mg of SAMe Ion/TABLET

Composition Based on SAMe Sulphate p-toluenesulphonate/Inositol/Inositol 6-phosphate

| | | |
|---|---|---|
| A. SAMe sulphate p-toluenesulphonate | 215.00 | mg |
| B. Inositol | 600.00 | mg |
| C. Inositol 6-phosphate | 400.00 | mg |
| C. Magnesium oxide | 50.00 | mg |
| D. Glyceryl behenate (Compritol-e-ato ®) | 100.00 | mg |
| E. Anhydrous microcrystalline cellulose | 70.00 | mg |
| F. Magnesium stearate | 10.00 | mg |
| Total weight of the core | 1445.00 | mg |
| G. Hydrogenated fatty acids | 8.00 | mg |
| H. Water-soluble Shellac ® | 30.00 | mg |
| I. PVP K 30 | 6.00 | mg |
| L. Titanium dioxide | 5.00 | mg |
| M. Talcum | 10.00 | mg |
| N. Triethyl citrate | 5.00 | mg |
| O. Riblofavin 6-phosphate | 0.050 | mg |
| Total weight of the tablet | 1509.05 | mg |

The amounts refer to the preparation of a standard industrial batch of 250.00 kg of tablets.

The tablets were prepared according to the procedure described in Example 1 using the components and amounts listed above.

EXAMPLE 3

Tablets Containing 100 mg of SAMe Ion/Tablet

Composition Based on SAMe Sulphate p-toluenesulphonate/Inositol/Inositol 6-phosphate

| | | |
|---|---|---|
| A. SAMe sulphate p-toluenesulphonate | 215.00 | mg |
| B. Inositol | 600.00 | mg |
| C. Inositol 6-phosphate | 400.00 | mg |
| D. Magnesium oxide | 50.00 | mg |
| E. Glyceryl behenate (Compritol-e-ato ®) | 100.00 | mg |
| F. Anhydrous microcrystalline cellulose | 70.00 | mg |
| G. Magnesium stearate | 10.00 | mg |
| H. Mannitol | 100.00 | mg |
| I. Hydrogenated fatty acids | 200.00 | mg |
| I. Aromas | 0.01 | mg |
| L. Sweeteners | 0.01 | mg |
| Total weight of the core | 1745.02 | mg |

The amounts refer to the preparation of a standard industrial batch of 250.00 kg of tablets.

The tablets were prepared according to the procedure described in Example 1 using the components and amounts listed above.

TABLE 3

Batch 056 - cores containing 100 mg of SAMe ion/tablet

| Batch (T/t)[1] | Moisture in % (K. Fischer) | AD[2] (%) | MTAD[3] (%) | SAMe[4] |
|---|---|---|---|---|
| 056 (20/0) | 1.00 | 0.35 | 0.46 | 104.11 |
| 056A (40/1) | 1.02 | 0.66 | 1.82 | 103.56 |
| 056B (40/3) | 1.04 | 0.85 | 2.45 | 100.23 |
| 056C (40/6) | 1.32 | 1.34 | 3.43 | 95.56 |

[1]Temperature (° C.)/time (months);
[2]adenosine;
[3]methylthioadenosine;
[4]SAMe sulphate p-toluenesulphonate (mg/tablet).

The data in Table 3 show that the tablets have optimum stability.

EXAMPLE 4

Tablets Containing 100 mg of SAMe Ion/Tablet

Composition Based on SAMe Sulphate p-toluenesulphonate/Inositol

| | | |
|---|---|---|
| A. SAMe sulphate p-toluenesulphonate | 215.00 | mg |
| B. Inositol | 1000.00 | mg |
| C. Magnesium oxide | 50.00 | mg |
| D. Glyceryl behenate (Compritol-e-ato ®) | 100.00 | mg |
| E. Anhydrous microcrystalline cellulose | 70.00 | mg |
| F. Magnesium stearate | 10.00 | mg |
| G. Mannitol | 100.00 | mg |
| H. Hydrogenated fatty acids | 200.00 | mg |
| I. Aromas | 0.01 | mg |
| L. Sweeteners | 0.01 | mg |
| Total weight of the core | 1745.02 | mg |

The amounts refer to the preparation of a standard industrial batch of 250.00 kg of tablets.

The tablets were prepared according to the procedure described in Example 1 using the components and amounts listed above.

EXAMPLE 5

Tablets Containing 100 mg of SAMe Ion/Tablet+St. John's Wort Extract

Composition Based on SAMe Sulphate p-toluenesulphonate/Inositol/St. John's Wort Extract

| | |
|---|---|
| A. SAMe sulphate p-toluenesulphonate | 215.00 mg |
| B. Inositol | 1000.00 mg |
| C. St. John's Wort extract | 100.00 mg |
| D. Magnesium oxide | 50.00 mg |
| E. Glyceryl behenate (Compritol-e-ato ®) | 100.00 mg |
| F. Anhydrous microcrystalline cellulose | 70.00 mg |
| G. Magnesium stearate | 10.00 mg |
| H. Mannitol | 100.00 mg |
| I. Hydrogenated fatty acids | 200.00 mg |
| L. Aromas | 0.01 mg |
| M. Sweeteners | 0.01 mg |
| Total weight of the core | 1845.02 mg |

The amounts refer to the preparation of a standard industrial batch of 250.00 kg of tablets.

The tablets were prepared according to the procedure described in Example 1 using the components and amounts listed above.

TABLE 4

Batch 057 cores containing 100 mg of SAMe ion/tablet

| Batch (T/t)[1] | Moisture in % (K.F.) | AD[2] (%) | MTAD[3] (%) | SAMe[4] mg/tablet | Hypericin mg |
|---|---|---|---|---|---|
| 057 (20/0) | 1.22 | 0.33 | 0.12 | 112.11 | 3.06 |
| 057A (40/1) | 1.12 | 0.54 | 0.45 | 102.23 | 2.94 |
| 057B (40/3) | 1.13 | 0.77 | 1.66 | 98.89 | 2.86 |
| 057C (40/6) | 1.07 | 1.45 | 2.99 | 95.44 | 2.77 |

[1]Temperature (° C.)/time (months);
[2]adenosine;
[3]methylthioadenosine;
[4]SAMe sulphate p-toluenesulphonate (mg/tablet).

The data from table 4 show that the tablets have optimum stability.

EXAMPLE 6

Tablets Containing 100 mg of SAMe Ion/Tablet+St. John's Wort Extract+Inositol 6-phosphate Composition Based on SAMe Sulphate p-toluenesulphonate/Inositol/Inositol 6-phosphate/St. John's Wort Extract

| | |
|---|---|
| A. SAMe sulphate p-toluenesulphonate | 215.00 mg |
| B. Inositol | 600.00 mg |
| C. Inositol 6-phosphate | 400.00 mg |
| D. St. John's Wort extract | 100.00 mg |
| E. Magnesium oxide | 50.00 mg |
| F. Glyceryl behenate (Compritol-e-ato ®) | 100.00 mg |
| G. Anhydrous microcrystalline cellulose | 70.00 mg |
| H. Magnesium stearate | 10.00 mg |
| I. Mannitol | 100.00 mg |
| L. Hydrogenated fatty acids | 200.00 mg |
| M. Aromas | 0.01 mg |
| N. Sweeteners | 0.01 mg |
| Total weight of the core | 1845.02 mg |

The amounts refer to the preparation of a standard industrial batch of 250.00 kg of tablets.

The tablets were prepared according to the procedure described in Example 1 using the components and amounts listed above.

TABLE 5

Batch 058 cores containing 100 mg of ion/tablet (EX. 5)

| Batch (T/t)[1] | Moisture in % (K.F.) | AD[2] (%) | MTAD[3] (%) | SAMe[4] mg/tablet | Hypericin mg | Inositol 6-phosphate |
|---|---|---|---|---|---|---|
| 058 (20/0) | 1.31 | 0.35 | 0.62 | 108.14 | 2.99 | 399.5 |
| 058A (40/1) | 1.18 | 0.64 | 0.85 | 100.23 | 2.7 | 398.6 |
| 058B (40/3) | 1.23 | 0.87 | 2.36 | 95.89 | 2.66 | 397.6 |
| 058C (40/6) | 1.24 | 1.99 | 3.79 | 93.54 | 2.70 | 395.5 |

[1]Temperature (° C.)/time (months);
[2]adenosine;
[3]methylthioadenosine;
[4]SAMe sulphate p-toluenesulphonate (mg/tablet).

The data in Table 5 show that the tablets have optimum stability

EXPERIMENTAL SECTION

Stability tests on the finished product. Both the stability at 40° C. 75% of r.h. (STRESS TEST) and the long-term stability at ambient temperature (SHELF LIFE) of the compositions from Examples 1, 2, 3, 4, 5, 6 obtainable by the process according to the invention were determined on the basis of variations in the appearance (mostly colour variations), the content (mg/tablet) in SAMe sulphate p-toluenesulphonate and other active components, the increase in degradation impurities and the moisture (K. F.); the presence of any degradation products substantially identifiable in adenosine and methylthioadenosine, expressed in percent, relative to mg of SAMe sulphate p-toluenesulphonate per tablet, was furthermore controlled by HPLC.

Stress Test

The tablets were packaged in closed and sealed glass vials, in order to reproduce the final packaging conditions (in general, alu/alu blister packs).

The samples thus prepared were kept for six months in an oven (Kottermann), thermostatted at a temperature of 40±2° C. and 75% of r.h.

Nine samples from three different batches were used for the 100 mg tablets (Ex. 1, 2, 3, 4, 5, 6) where each sample, in each batch, was sampled after 0, 1, 3 and 6 months.

The results of the stress test are shown in the tables below (6-23).

TABLE 6

Batch 059A - tablets containing 100 mg of ion/tablet (EX. 1)

| Batch (T/t)[1] | Moisture in % (K. Fischer) | AD[2] (%) | MTAD[3] (%) | SAMe[4] |
|---|---|---|---|---|
| 059 (20/0) | 1.38 | 0.31 | 0.41 | 112.42 |
| 059A (40/1) | 1.26 | 1.14 | 1.75 | 111.19 |
| 059B (40/3) | 1.54 | 1.95 | 2.18 | 109.12 |
| 059C (40/6) | 1.46 | 2.01 | 2.61 | 105.67 |

[1]Temperature (° C.)/time (months);
[2]adenosine;
[3]methylthioadenosine;
[4]SAMe sulphate p-toluenesulphonate (mg/tablet).

TABLE 7

Batch 060 - tablets containing 100 mg of ion/tablet (EX. 1)

| Batch (T/t)[1] | Moisture in % (K. Fischer) | AD[2] (%) | MTAD[3] (%) | SAMe[4] |
|---|---|---|---|---|
| 060 (20/0) | 1.56 | 0.31 | 0.27 | 113.93 |
| 060A (40/1) | 1.61 | 1.05 | 1.89 | 109.78 |
| 060B (40/3) | 1.49 | 1.72 | 2.37 | 105.37 |
| 060C (40/6) | 1.41 | 1.84 | 2.53 | 103.67 |

[1]Temperature (° C.)/time (months);
[2]adenosine;
[3]methylthioadenosine;
[4]SAMe sulphate p-toluenesulphonate (mg/tablet).

TABLE 8

Batch 061 - tablets containing 100 mg of ion/tablet (EX. 1)

| Batch (T/t)[1] | Moisture in % (K. Fischer) | AD[2] (%) | MTAD[3] (%) | SAMe[4] |
|---|---|---|---|---|
| 061 (20/0) | 1.30 | 0.47 | 0.42 | 113.43 |
| 061A (40/1) | 1.56 | 1.04 | 1.00 | 109.19 |
| 061B (40/3) | 1.45 | 1.78 | 2.36 | 107.36 |
| 061C (40/6) | 1.53 | 2.32 | 2.20 | 105.43 |

[1]Temperature (° C.)/time (months);
[2]adenosine;
[3]methylthioadenosine;
[4]SAMe sulphate p-toluenesulphonate (mg/tablet).

TABLE 9

Batch 062 - tablets containing 100 mg of ion/tablet (EX. 2)

| Batch (T/t)[1] | Moisture in % (K. Fischer) | AD[2] (%) | MTAD[3] (%) | SAMe[4] |
|---|---|---|---|---|
| 062 (20/0) | 1.39 | 0.42 | 0.38 | 111.60 |
| 062A (40/1) | 1.58 | 1.81 | 1.15 | 110.9 |
| 062B (40/3) | 1.23 | 1.78 | 2.05 | 108.62 |
| 062C (40/6) | 1.60 | 2.03 | 2.41 | 106.51 |

[1]Temperature (° C.)/time (months);
[2]adenosine;
[3]methylthioadenosine;
[4]SAMe sulphate p-toluenesulphonate (mg/tablet).

TABLE 10

Batch 063 tablets containing 100 mg of ion/tablet (EX. 2)

| Batch (T/t)[1] | Moisture in % (K. Fischer) | AD[2] (%) | MTAD[3] (%) | SAMe[4] |
|---|---|---|---|---|
| 063 (20/0) | 1.11 | 0.34 | 0.56 | 116.22 |
| 063 (40/1) | 1.18 | 1.21 | 1.23 | 113.43 |
| 063 (40/3) | 1.08 | 1.63 | 1.45 | 109.16 |
| 063 (40/6) | 1.21 | 2.01 | 2.39 | 107.21 |

[1]Temperature (° C.)/time (months);
[2]adenosine;
[3]methylthioadenosine;
[4]SAMe sulphate p-toluenesulphonate (mg/tablet).

TABLE 11

Batch 064 - tablets containing 100 mg of ion/tablet (EX. 2)

| Batch (T/t)[1] | Moisture in % (K. Fischer) | AD[2] (%) | MTAD[3] (%) | SAMe[4] |
|---|---|---|---|---|
| 064 (20/0) | 1.32 | 0.29 | 0.53 | 111.20 |
| 064A (40/1) | 1.23 | 1.04 | 1.01 | 108.30 |
| 064B (40/3) | 1.17 | 1.23 | 1.36 | 106.25 |
| 064C (40/6) | 1.15 | 1.89 | 2.45 | 105.20 |

[1]Temperature (° C.)/time (months);
[2]adenosine;
[3]methylthioadenosine;
[4]SAMe sulphate p-toluenesulphonate (mg/tablet).

TABLE 12

Batch 065 - tablets containing 100 mg of ion/tablet (EX. 3)

| Batch (T/t)[1] | Moisture in % (K. Fischer) | AD[2] (%) | MTAD[3] (%) | SAMe[4] |
|---|---|---|---|---|
| 065 (20/0) | 1.31 | 0.32 | 0.24 | 112.60 |
| 065A (40/1) | 1.28 | 1.23 | 1.02 | 111.9 |
| 065B (40/3) | 1.43 | 1.54 | 1.45 | 108.62 |
| 065C (40/6) | 1.23 | 1.93 | 2.02 | 107.45 |

[1]Temperature (° C.)/time (months);
[2]adenosine;
[3]methylthioadenosine;
[4]SAMe sulphate p-toluenesulphonate (mg/tablet).

TABLE 13

Batch 066 tablets containing 100 mg of ion/tablet (EX. 3)

| Batch (T/t)[1] | Moisture in % (K. Fischer) | AD[2] (%) | MTAD[3] (%) | SAMe[4] |
|---|---|---|---|---|
| 066 (20/0) | 1.11 | 0.34 | 0.46 | 113.22 |
| 066 (40/1) | 1.13 | 1.21 | 1.01 | 111.43 |
| 066 (40/3) | 1.18 | 1.56 | 1.35 | 109.45 |
| 066 (40/6) | 1.22 | 2.11 | 1.99 | 107.98 |

[1]Temperature (° C.)/time (months);
[2]adenosine;
[3]methylthioadenosine;
[4]SAMe sulphate p-toluenesulphonate (mg/tablet).

TABLE 14

Batch 067 - tablets containing 100 mg of ion/tablet (EX. 3)

| Batch (T/t)[1] | Moisture in % (K. Fischer) | AD[2] (%) | MTAD[3] (%) | SAMe[4] |
|---|---|---|---|---|
| 067 (20/0) | 1.23 | 0.29 | 0.32 | 110.20 |
| 067A (40/1) | 1.24 | 1.14 | 0.95 | 107.30 |
| 067B (40/3) | 1.17 | 1.45 | 1.34 | 106.25 |
| 067C (40/6) | 1.35 | 1.99 | 1.78 | 104.43 |

[1]Temperature (° C.)/time (months);
[2]adenosine;
[3]methylthioadenosine;
[4]SAMe sulphate p-toluenesulphonate (mg/tablet).

TABLE 15

Batch 068 - tablets containing 100 mg of ion/tablet (EX. 4)

| Batch (T/t)[1] | Moisture in % (K. Fischer) | AD[2] (%) | MTAD[3] (%) | SAMe[4] |
|---|---|---|---|---|
| 068 (20/0) | 1.33 | 0.32 | 0.42 | 109.45 |
| 068A (40/1) | 1.26 | 1.01 | 0.76 | 108.9 |
| 068B (40/3) | 1.65 | 1.44 | 1.35 | 10562 |
| 068C (40/6) | 1.46 | 1.50 | 1.87 | 103.87 |

[1]Temperature (° C.)/time (months);
[2]adenosine;
[3]methylthioadenosine;
[4]SAMe sulphate p-toluenesulphonate (mg/tablet).

TABLE 16

Batch 069 tablets containing 100 mg of ion/tablet (EX. 4)

| Batch (T/t)[1] | Moisture in % (K. Fischer) | AD[2] (%) | MTAD[3] (%) | SAMe[4] |
|---|---|---|---|---|
| 069 (20/0) | 1.33 | 0.37 | 0.39 | 107.05 |
| 069A (40/1) | 1.44 | 1.02 | 0.99 | 106.43 |
| 069B (40/3) | 1.53 | 1.67 | 1.54 | 105.69 |
| 069C (40/6) | 1.50 | 2.43 | 1.97 | 103.45 |

[1]Temperature (° C.)/time (months);
[2]adenosine;
[3]methylthioadenosine;
[4]SAMe sulphate p-toluenesulphonate (mg/tablet).

TABLE 17

Batch 070 - tablets containing 100 mg of ion/tablet (EX. 4)

| Batch (T/t)[1] | Moisture in % (K. Fischer) | AD[2] (%) | MTAD[3] (%) | SAMe[4] |
|---|---|---|---|---|
| 070 (20/0) | 1.45 | 0.20 | 0.42 | 110.34 |
| 070A (40/1) | 1.65 | 1.34 | 0.94 | 108.54 |
| 070B (40/3) | 1.53 | 1.75 | 1.39 | 106.34 |
| 070C (40/6) | 1.49 | 2.09 | 1.98 | 104.96 |

[1]Temperature (° C.)/time (months);
[2]adenosine;
[3]methylthioadenosine;
[4]SAMe sulphate p-toluenesulphonate (mg/tablet).

TABLE 18

Batch 071 - tablets containing 100 mg of ion/tablet (EX. 5)

| Batch (T/t)[1] | Moisture in % (K. Fischer) | AD[2] (%) | MTAD[3] (%) | SAMe[4] |
|---|---|---|---|---|
| 071 (20/0) | 1.44 | 0.39 | 0.53 | 112.45 |
| 071A (40/1) | 1.46 | 1.11 | 1.46 | 110.34 |
| 071B (40/3) | 1.63 | 1.45 | 1.65 | 107.65 |
| 071C (40/6) | 1.56 | 1.80 | 2.37 | 105.99 |

[1]Temperature (° C.)/time (months);
[2]adenosine;
[3]methylthioadenosine;
[4]SAMe sulphate p-toluenesulphonate (mg/tablet).

TABLE 19

Batch 072 tablets containing 100 mg of ion/tablet (EX. 5)

| Batch (T/t)[1] | Moisture in % (K. Fischer) | AD[2] (%) | MTAD[3] (%) | SAMe[4] |
|---|---|---|---|---|
| 072 (20/0) | 1.61 | 0.29 | 0.41 | 109.56 |
| 072A (40/1) | 1.76 | 0.76 | 0.79 | 107.67 |
| 072B (40/3) | 1.53 | 1.37 | 1.44 | 105.69 |
| 072C (40/6) | 1.61 | 2.02 | 1.85 | 103.69 |

[1]Temperature (° C.)/time (months);
[2]adenosine;
[3]methylthioadenosine;
[4]SAMe sulphate p-toluenesulphonate (mg/tablet).

TABLE 20

Batch 073 - tablets containing 100 mg of ion/tablet (EX. 5)

| Batch (T/t)[1] | Moisture in % (K. Fischer) | AD[2] (%) | MTAD[3] (%) | SAMe[4] |
|---|---|---|---|---|
| 073 (20/0) | 1.45 | 0.23 | 0.34 | 110.33 |
| 073A (40/1) | 1.62 | 1.54 | 0.92 | 108.52 |
| 073B (40/3) | 1.54 | 1.85 | 1.49 | 105.74 |
| 073C (40/6) | 1.67 | 2.39 | 1.88 | 103.95 |

[1]Temperature (° C.)/time (months);
[2]adenosine;
[3]methylthioadenosine;
[4]SAMe sulphate p-toluenesulphonate (mg/tablet).

TABLE 21

Batch 074 - tablets containing 100 mg of ion/tablet (EX. 6)

| Batch (T/t)[1] | Moisture in % (K. Fischer) | AD[2] (%) | MTAD[3] (%) | SAMe[4] |
|---|---|---|---|---|
| 074 (20/0) | 1.44 | 0.39 | 0.34 | 111.23 |
| 074A (40/1) | 1.66 | 1.41 | 0.87 | 110.34 |
| 074B (40/3) | 1.69 | 1.75 | 1.45 | 107.23 |
| 074C (40/6) | 1.54 | 1.89 | 2.12 | 104.59 |

[1]Temperature (° C.)/time (months);
[2]adenosine;
[3]methylthioadenosine;
[4]SAMe sulphate p-toluenesulphonate (mg/tablet).

TABLE 22

Batch 075 tablets containing 100 mg of ion/tablet (EX. 6)

| Batch (T/t)[1] | Moisture in % (K. Fischer) | AD[2] (%) | MTAD[3] (%) | SAMe[4] |
|---|---|---|---|---|
| 075 (20/0) | 1.46 | 0.43 | 0.45 | 109.56 |
| 075A (40/1) | 1.66 | 0.83 | 0.98 | 107.67 |
| 075B (40/3) | 1.59 | 1.47 | 1.54 | 105.69 |
| 075C (40/6) | 1.63 | 2.32 | 1.99 | 103.69 |

[1]Temperature (° C.)/time (months);
[2]adenosine;
[3]methylthioadenosine;
[4]SAMe sulphate p-toluenesulphonate (mg/tablet).

TABLE 23

Batch 076 - tablets containing 100 mg of ion/tablet (EX. 6)

| Batch (T/t)[1] | Moisture in % (K. Fischer) | AD[2] (%) | MTAD[3] (%) | SAMe[4] |
|---|---|---|---|---|
| 076 (20/0) | 1.56 | 0.27 | 0.34 | 114.63 |
| 0763A (40/1) | 1.62 | 1.64 | 0.87 | 112.52 |
| 076B (40/3) | 1.59 | 1.89 | 1.67 | 110.54 |
| 076C (40/6) | 1.69 | 2.39 | 2.28 | 108.56 |

[1]Temperature (° C.)/time (months);
[2]adenosine;
[3]methylthioadenosine;
[4]SAMe sulphate p-toluenesulphonate (mg/tablet).

From the stability data at 40° C. and 75% of r.h. (stress test), it can be seen that after six months all batches tested were subject to a degradation of about 5% both in terms of SAMe and the other active components.

Shelf Life

The tablets were packaged in closed and sealed glass vials, in order to reproduce the final packaging conditions (in general, alu/alu blister packs).

The samples were selected using the same method and amounts described for the stress test and kept in a thermostatted environment at a temperature of 25±2° C. and a humidity of 60% of r.h.

Nine samples from three different batches were used for the 100 mg tablets (Ex. 1, 2, 3, 4, 5, 6) where each sample, in each batch, was sampled after 0, 3, 6, and 12 months.

The results of the shelf life test are shown in the tables below (24-41).

TABLE 24

Batch 077A - tablets containing 100 mg of ion/tablet (EX. 1)

| Batch (T/t)[1] | Moisture in % (K. Fischer) | AD[2] (%) | MTAD[3] (%) | SAMe[4] |
|---|---|---|---|---|
| 077 (20/0) | 1.38 | 0.31 | 0.41 | 112.42 |
| 077A (25/3) | 1.29 | 0.54 | 1.45 | 112.19 |
| 077B (25/6) | 1.44 | 0.64 | 2.11 | 111.54 |
| 077C (25/12) | 1.48 | 0.89 | 2.21 | 110.57 |

[1]Temperature (° C.)/time (months);
[2]adenosine;
[3]methylthioadenosine;
[4]SAMe sulphate p-toluenesulphonate (mg/tablet).

TABLE 25

Batch 078 - tablets containing 100 mg of ion/tablet (EX. 1)

| Batch (T/t)[1] | Moisture in % (K. Fischer) | AD[2] (%) | MTAD[3] (%) | SAMe[4] |
|---|---|---|---|---|
| 078 (20/0) | 1.56 | 0.31 | 0.27 | 113.93 |
| 078A (25/1) | 1.41 | 0.55 | 0.49 | 113.78 |
| 078B (25/3) | 1.46 | 0.72 | 0.77 | 112.37 |
| 078C (25/6) | 1.51 | 0.84 | 0.93 | 111.67 |

[1]Temperature (° C.)/time (months);
[2]adenosine;
[3]methylthioadenosine;
[4]SAMe sulphate p-toluenesulphonate (mg/tablet).

TABLE 26

Batch 079 - tablets containing 100 mg of ion/tablet (EX. 1)

| Batch (T/t)[1] | Moisture in % (K. Fischer) | AD[2] (%) | MTAD[3] (%) | SAMe[4] |
|---|---|---|---|---|
| 079 (20/0) | 1.30 | 0.47 | 0.42 | 113.43 |
| 079A (25/1) | 1.66 | 0.64 | 0.78 | 111.99 |
| 079B (25/3) | 1.55 | 0.78 | 0.89 | 111.09 |
| 079C (25/6) | 1.58 | 1.32 | 1.20 | 110.32 |

[1]Temperature (° C.)/time (months);
[2]adenosine;
[3]methylthioadenosine;
[4]SAMe sulphate p-toluenesulphonate (mg/tablet).

TABLE 27

Batch 080 - tablets containing 100 mg of ion/tablet (EX. 2)

| Batch (T/t)[1] | Moisture in % (K. Fischer) | AD[2] (%) | MTAD[3] (%) | SAMe[4] |
|---|---|---|---|---|
| 080 (20/0) | 1.39 | 0.42 | 0.38 | 111.60 |
| 080A (25/1) | 1.58 | 0.71 | 0.55 | 111.79 |
| 080B (25/3) | 1.23 | 1.02 | 0.78 | 109.92 |
| 080C (25/6) | 1.60 | 1.33 | 0.91 | 109.51 |

[1]Temperature (° C.)/time (months);
[2]adenosine;
[3]methylthioadenosine;
[4]SAMe sulphate p-toluenesulphonate (mg/tablet).

TABLE 28

Batch 081 tablets containing 100 mg of ion/tablet (EX. 2)

| Batch (T/t)[1] | Moisture in % (K. Fischer) | AD[2] (%) | MTAD[3] (%) | SAMe[4] |
|---|---|---|---|---|
| 081 (20/0) | 1.11 | 0.34 | 0.56 | 116.22 |
| 081 (25/1) | 1.28 | 0.41 | 0.55 | 115.43 |
| 081 (25/3) | 1.38 | 0.63 | 0.85 | 115.00 |
| 081 (25/6) | 1.31 | 0.81 | 1.39 | 114.21 |

[1]Temperature (° C.)/time (months);
[2]adenosine;
[3]methylthioadenosine;
[4]SAMe sulphate p-toluenesulphonate (mg/tablet).

TABLE 29

Batch 082 - tablets containing 100 mg of ion/tablet (EX. 2)

| Batch (T/t)[1] | Moisture in % (K. Fischer) | AD[2] (%) | MTAD[3] (%) | SAMe[4] |
|---|---|---|---|---|
| 082 (20/0) | 1.32 | 0.29 | 0.53 | 111.20 |
| 082A (25/1) | 1.33 | 0.44 | 0.61 | 110.30 |
| 082B 250/3) | 1.37 | 0.63 | 0.76 | 110.25 |
| 082C (25/6) | 1.45 | 0.89 | 1.25 | 109.48 |

[1]Temperature (° C.)/time (months);
[2]adenosine;
[3]methylthioadenosine;
[4]SAMe sulphate p-toluenesulphonate (mg/tablet).

TABLE 30

Batch 083 - tablets containing 100 mg of ion/tablet (EX. 3)

| Batch (T/t)[1] | Moisture in % (K. Fischer) | AD[2] (%) | MTAD[3] (%) | SAMe[4] |
|---|---|---|---|---|
| 083 (20/0) | 1.31 | 0.32 | 0.24 | 112.60 |
| 083A (25/1) | 1.48 | 0.34 | 0.42 | 110.42 |
| 083B (25/3) | 1.42 | 0.54 | 0.45 | 111.12 |
| 083C (25/6) | 1.53 | 0.83 | 1.02 | 110.21 |

[1]Temperature (° C.)/time (months);
[2]adenosine;
[3]methylthioadenosine;
[4]SAMe sulphate p-toluenesulphonate (mg/tablet).

TABLE 31

Batch 084 tablets containing 100 mg of ion/tablet (EX. 3)

| Batch (T/t)[1] | Moisture in % (K. Fischer) | AD[2] (%) | MTAD[3] (%) | SAMe[4] |
|---|---|---|---|---|
| 084 (20/0) | 1.11 | 0.34 | 0.46 | 113.22 |
| 084A (25/1) | 1.33 | 0.41 | 0.66 | 112.43 |
| 084B (25/3) | 1.28 | 0.56 | 0.85 | 111.45 |
| 084C (25/6) | 1.12 | 0.89 | 0.99 | 111.28 |

[1]Temperature (° C.)/time (months);
[2]adenosine;
[3]methylthioadenosine;
[4]SAMe sulphate p-toluenesulphonate (mg/tablet).

TABLE 32

Batch 085 - tablets containing 100 mg of ion/tablet (EX. 3)

| Batch (T/t)[1] | Moisture in % (K. Fischer) | AD[2] (%) | MTAD[3] (%) | SAMe[4] |
|---|---|---|---|---|
| 085 (20/0) | 1.23 | 0.29 | 0.32 | 110.20 |
| 085A (25/1) | 1.14 | 0.34 | 0.55 | 109.50 |
| 085B (25/3) | 1.17 | 0.45 | 0.74 | 108.25 |
| 085C (25/6) | 1.15 | 0.69 | 0.79 | 107.34 |

[1]Temperature (° C.)/time (months);
[2]adenosine;
[3]methylthioadenosine;
[4]SAMe sulphate p-toluenesulphonate (mg/tablet).

TABLE 33

Batch 086 - tablets containing 100 mg of ion/tablet (EX. 4)

| Batch (T/t)[1] | Moisture in % (K. Fischer) | AD[2] (%) | MTAD[3] (%) | SAMe[4] |
|---|---|---|---|---|
| 086 (20/0) | 1.33 | 0.32 | 0.42 | 109.45 |
| 086A (25/1) | 1.21 | 0.44 | 0.76 | 108.44 |
| 086B (25/3) | 1.25 | 0.44 | 0.88 | 108.32 |
| 086C (25/6) | 1.16 | 0.50 | 0.98 | 107.34 |

[1]Temperature (° C.)/time (months);
[2]adenosine;
[3]methylthioadenosine;
[4]SAMe sulphate p-toluenesulphonate (mg/tablet).

TABLE 34

Batch 087 tablets containing 100 mg of ion/tablet (EX. 4)

| Batch (T/t)[1] | Moisture in % (K. Fischer) | AD[2] (%) | MTAD[3] (%) | SAMe[4] |
|---|---|---|---|---|
| 087 (20/0) | 1.33 | 0.37 | 0.39 | 107.05 |
| 087A (25/1) | 1.12 | 0.32 | 0.59 | 107.43 |
| 087B (25/3) | 1.13 | 0.43 | 0.54 | 106.69 |
| 087C (25/6) | 1.23 | 0.73 | 0.93 | 106.11 |

[1]Temperature (° C.)/time (months);
[2]adenosine;
[3]methylthioadenosine;
[4]SAMe sulphate p-toluenesulphonate (mg/tablet).

TABLE 35

Batch 088 - tablets containing 100 mg of ion/tablet (EX. 4)

| Batch (T/t)[1] | Moisture in % (K. Fischer) | AD[2] (%) | MTAD[3] (%) | SAMe[4] |
|---|---|---|---|---|
| 088 (20/0) | 1.45 | 0.20 | 0.42 | 110.34 |
| 088A (25/1) | 1.35 | 0.34 | 0.64 | 110.54 |
| 088B (25/3) | 1.23 | 0.65 | 0.59 | 109.34 |
| 088C (25/6) | 1.39 | 0.69 | 0.58 | 108.56 |

[1]Temperature (° C.)/time (months);
[2]adenosine;
[3]methylthioadenosine;
[4]SAMe sulphate p-toluenesulphonate (mg/tablet).

TABLE 36

Batch 089 - tablets containing 100 mg of ion/tablet (EX. 5)

| Batch (T/t)[1] | Moisture in % (K. Fischer) | AD[2] (%) | MTAD[3] (%) | SAMe[4] |
|---|---|---|---|---|
| 089(0/0) | 1.44 | 0.39 | 0.53 | 112.45 |
| 089A (25/1) | 1.22 | 0.53 | 0.66 | 112.33 |
| 089B (25/3) | 1.31 | 0.65 | 0.73 | 111.65 |
| 089C (25/6) | 1.22 | 0.84 | 0.95 | 110.59 |

[1]Temperature (° C.)/time (months);
[2]adenosine;
[3]methylthioadenosine;
[4]SAMe sulphate p-toluenesulphonate (mg/tablet).

TABLE 37

Batch 090 tablets containing 100 mg of ion/tablet (EX. 5)

| Batch (T/t)[1] | Moisture in % (K. Fischer) | AD[2] (%) | MTAD[3] (%) | SAMe[4] |
|---|---|---|---|---|
| 090 (20/0) | 1.61 | 0.29 | 0.41 | 109.56 |
| 090A (25/1) | 1.33 | 0.56 | 0.59 | 108.67 |
| 090B (25/3) | 1.45 | 0.77 | 0.74 | 107.69 |
| 090C (25/6) | 1.41 | 0.92 | 0.85 | 106.44 |

[1]Temperature (° C.)/time (months);
[2]adenosine;
[3]methylthioadenosine;
[4]SAMe sulphate p-toluenesulphonate (mg/tablet).

TABLE 38

Batch 091 - tablets containing 100 mg of ion/tablet (EX. 5)

| Batch (T/t)[1] | Moisture in % (K. Fischer) | AD[2] (%) | MTAD[3] (%) | SAMe[4] |
|---|---|---|---|---|
| 091 (20/0) | 1.45 | 0.23 | 0.34 | 110.33 |
| 091A (25/1) | 1.42 | 0.54 | 0.52 | 109.52 |
| 091B (25/3) | 1.34 | 0.85 | 0.49 | 108.74 |
| 091C (25/6) | 1.47 | 1.39 | 0.88 | 106.95 |

[1]Temperature (° C.)/time (months);
[2]adenosine;
[3]methylthioadenosine;
[4]SAMe sulphate p-toluenesulphonate (mg/tablet).

TABLE 39

Batch 092 - tablets containing 100 mg of ion/tablet (EX. 6)

| Batch (T/t)[1] | Moisture in % (K. Fischer) | AD[2] (%) | MTAD[3] (%) | SAMe[4] |
|---|---|---|---|---|
| 092 (20/0) | 1.44 | 0.39 | 0.34 | 111.23 |
| 092A (25/1) | 1.36 | 0.41 | 0.67 | 110.11 |
| 092B (25/3) | 1.49 | 0.55 | 0.75 | 109.44 |
| 092C (25/6) | 1.23 | 0.89 | 1.12 | 109.49 |

[1]Temperature (° C.)/time (months);
[2]adenosine;
[3]methylthioadenosine;
[4]SAMe sulphate p-toluenesulphonate (mg/tablet).

TABLE 40

Batch 093 tablets containing 100 mg of ion/tablet (EX. 6)

| Batch (T/t)[1] | Moisture in % (K. Fischer) | AD[2] (%) | MTAD[3] (%) | SAMe[4] |
|---|---|---|---|---|
| 093 (20/0) | 1.46 | 0.43 | 0.45 | 109.56 |
| 093A (25/1) | 1.32 | 0.53 | 0.58 | 108.99 |
| 093B (25/3) | 1.21 | 0.67 | 0.54 | 108.69 |
| 093C (25/6) | 1.23 | 1.12 | 0.89 | 107.69 |

[1]Temperature (° C.)/time (months);
[2]adenosine;
[3]methylthioadenosine;
[4]SAMe sulphate p-toluenesulphonate (mg/tablet).

TABLE 41

Batch 094 - tablets containing 100 mg of ion/tablet (EX. 6)

| Batch (T/t)[1] | Moisture in % (K. Fischer) | AD[2] (%) | MTAD[3] (%) | SAMe[4] |
|---|---|---|---|---|
| 094 (20/0) | 1.56 | 0.27 | 0.34 | 114.63 |
| 094A (25/1) | 1.44 | 0.64 | 0.87 | 113.52 |
| 076B (25/3) | 1.34 | 0.87 | 1.67 | 112.54 |
| 094C (25/6) | 1.32 | 1.39 | 2.28 | 112.76 |

[1]Temperature (° C.)/time (months);
[2]adenosine;
[3]methylthioadenosine;
[4]SAMe sulphate p-toluenesulphonate (mg/tablet).

From the stability data at 25° C. and 60% of r.h. (shelf life), it can be seen that after twelve months all batches tested were subject to a very low degradation in terms of SAMe.

The purpose of the foregoing Abstract is to enable the public, and especially the scientists, engineers, and practitioners in the art who are not familiar with patent or legal terms or phraseology, to determine quickly from a cursory inspection, the nature and essence of the technical disclosure of the application. The Abstract is neither intended to define the invention, which is measured by the claims, nor is it intended to be limiting as to the scope of the invention in any way.

Still other features and advantages of the present invention will become readily apparent to those skilled in this art from the following detailed description describing only the preferred embodiment of the invention, simply by way of illustration of the best mode contemplated by carrying out my invention. As will be realized, the invention is capable of modification in various obvious respects all without departing from the invention. Accordingly, the description of the preferred embodiment is to be regarded as illustrative in nature, and not as restrictive in nature.

What is claimed is:

1. Dietary and/or nutraceutic oral pharmaceutical composition comprising S-adenosylmethionine (SAMe) or salts thereof in combination with inositol and/or derivatives thereof and pharmaceutically acceptable excipients, wherein at least one of the pharmaceutically acceptable excipients is magnesium oxide, wherein said magnesium oxide is present in an amount ranging from about 1.0% to about 10% by weight, wherein said magnesium oxide stabilizes said SAMe or salts thereof in said composition.

2. Composition according to claim 1, in which said SAMe is S-adenosylmethionine para-toluenesulphonate.

3. Composition according to claim 1, in which said inositol and/or derivatives is inositol on its own, inositol 6-phosphate or a mixture thereof.

4. Composition according to claim 1, in which the SAMe is contained in an amount which varies from about 10 to about 90% by weight, relative to the weight of the composition.

5. Composition according to claim 4, in which the SAMe is contained in an amount which varies from about 10 to 50% by weight, relative to the weight of the composition.

6. Composition according to claim 1, in which the inositol and/or derivatives thereof is contained in an amount which varies from about 50 to about 90% by weight, relative to the weight of the composition.

7. Composition according to claim 1, in which the inositol and/or derivatives thereof is contained in an amount which varies from about 30 to about 85% by weight, relative to the weight of the composition.

8. Composition according to claim 1, comprising at least one other active component, wherein said active component is selected from the group consisting of St. John's Wort dry extract, lemon balm dry extract, and mixtures thereof.

9. Composition according to claim 1, in the form of a tablet, capsule, granule or powder.

10. Composition according to claim 1, in the form of a tablet.

11. Composition according to claim 1, characterized in that it is in the form of a gastroresistant tablet.

12. Process for the preparation of a tablet according to claim 1, which comprises the steps of:
   a) mixing SAMe, or salts thereof, with pharmaceutically acceptable excipients;
   b) pre-compression, followed by granulation, of the mixture obtained in step a);
   c) coating the granulated product obtained in step b) with hydrogenated fatty acids;
   d) mixing, pre-compression and granulation of the inositol and/or derivatives thereof with pharmaceutically acceptable excipients;
   e) coating of the granulated products obtained in step d) with hydrogenated fatty acids;
   f) mixing the granulated products obtained in steps c) and e) with pharmaceutically acceptable excipients;
   g) compressing the mixture obtained in step f) with the optional addition of sweeteners and aromas;
   h) optionally coating the tablets obtained in step g) with hydrogenated fatty acids;
   i) optionally film-coating in the aqueous phase the tablets obtained in step h).

13. Process according to claim 12, in which SAMe is S-adenosylmethionine para-toluenesulphonate.

14. Process according to claim 12, in which said inositol and/or derivatives thereof is inositol on its own, inositol 6-phosphate or a mixture thereof.

15. Process according to claim 12, in which the relative humidity is below about 25% and the temperature is maintained between about 20° C. and 30° C., in particular at about 25° C.

16. Process according to claim 12, in which in step d) it is possible to add, to the mixture, at least one other active component, preferably selected from St. John's Wort dry extract and lemon balm dry extract and/or mixtures thereof.

17. Process according to claim 12, in which the coating carried out in step h) is effected with hydrogenated fatty acids in an amount of between 0.5 and 2.5% by weight, relative to the weight of the composition.

18. Process according to claim 1, in which the film-coating in the aqueous phase carried out in step i) is effected with a varnish, preferably selected from rubber varnish and/or salts thereof (Shellac™), methacrylic acid, cellulose acetophthalates, titanium dioxide, talcum, triethyl citrate, PVP K30, riboflavin 6-phosphate, hydroxypropylcellulose, hydroxypropylmethyl-cellulose and/or mixtures thereof.

19. Process according to claim 18, in which the varnish is contained in an amount ranging from about 2.0 to about 8.0% by weight, relative to the composition.

20. Process according to claim 1, in which in step i) it is possible to optionally add lemon balm and/or St. John's Wort oil in an amount which varies from about 0.01 to about 0.2% by weight, relative to the total composition.

21. A method of using a dietary and/or nutraceutic oral pharmaceutical composition comprising S-adenosylmethionine (SAMe) or salts thereof in combination with inositol and/or derivatives thereof and pharmaceutically acceptable excipients, wherein at least one of the pharmaceutically acceptable excipients is magnesium oxide, wherein said magnesium oxide is present in an amount ranging from about 1.0% to about 10% by weight, wherein said magnesium oxide stabilizes said SAMe or salts thereof in said composition for the treatment of depressive states and panic syndromes.

22. The method of claim 21, in which said SAMe is S-adenosylmethionine para-toluenesulphonate.

23. The method of to claim 21, in which said inositol and/or derivatives thereof is inositol on its own, inositol 6-phosphate or a mixture thereof.

24. Method of stabilising a solid dietary and/or nutraceutic pharmaceutical composition based on SAMe or salts thereof, which comprises using inositol and/or derivatives thereof and pharmaceutically acceptable excipients, wherein at least one of the pharmaceutically acceptable excipients is magnesium oxide, wherein said magnesium oxide is present in an amount ranging from about 1.0% to about 10% by weight, wherein said magnesium oxide stabilizes said SAMe or salts thereof in said composition.

25. Method according to claim 24, in which the SAMe or salts thereof is contained in an amount of between about 10 and about 90% by weight, calculated relative to the weight of the composition.

26. Method according to claim 25, in which the SAMe or salts thereof is contained in an amount of between about 10 and about 50% by weight, calculated relative to the weight of the composition.

27. Method according to claim 24, in which the inositol and/or derivatives thereof is contained in an amount which varies from about 50 to about 90% by weight, relative to the weight of the composition.

28. Method according to claim 27, in which the inositol and/or derivatives thereof is contained in an amount which varies from about 50 to about 85% by weight, relative to the weight of the composition.

* * * * *